United States Patent
Aoki et al.

(10) Patent No.: US 11,097,126 B2
(45) Date of Patent: Aug. 24, 2021

(54) ACCELERATOR AND PARTICLE THERAPY SYSTEM

(71) Applicant: Hitachi, Ltd., Tokyo (JP)

(72) Inventors: Takamichi Aoki, Tokyo (JP); Yuto Nakashima, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 16/755,630

(22) PCT Filed: Oct. 9, 2018

(86) PCT No.: PCT/JP2018/037622
§ 371 (c)(1),
(2) Date: Apr. 13, 2020

(87) PCT Pub. No.: WO2019/097904
PCT Pub. Date: May 23, 2019

(65) Prior Publication Data
US 2020/0330793 A1   Oct. 22, 2020

(30) Foreign Application Priority Data
Nov. 20, 2017   (JP) .............................. JP2017-222577

(51) Int. Cl.
*A61N 5/10* (2006.01)
*H05H 13/02* (2006.01)
(Continued)

(52) U.S. Cl.
CPC .............. *A61N 5/10* (2013.01); *H05H 13/005* (2013.01); *H05H 13/02* (2013.01); *H05H 13/04* (2013.01);
(Continued)

(58) Field of Classification Search
None
See application file for complete search history.

(56) References Cited

U.S. PATENT DOCUMENTS 8,067,748 B2 * 11/2011 Balakin .................. H05H 13/04
250/396 ML
8,084,965 B2 * 12/2011 Takayama .............. H05H 13/04
315/503
(Continued)

FOREIGN PATENT DOCUMENTS

JP    2005-302734 A1   10/2005
JP    2015-084886 A     5/2015
(Continued)

OTHER PUBLICATIONS

International Search Report, dated Dec. 11, 2018, which issued during the prosecution of International Application No. PCT/JP2018/037622, which corresponds to the present application.

*Primary Examiner* — Amy Cohen Johnson
*Assistant Examiner* — Srinivas Sathiraju
(74) *Attorney, Agent, or Firm* — Baker Botts L.L.P.

(57) ABSTRACT

An accelerator includes: a plurality of ion sources 221, 222, and 233 that generate a plurality of different types of ions; an electromagnet 11 that generates a magnetic field; and a high frequency cavity 21 that generates a high frequency electric field. The center of an orbit of the ion is eccentric with acceleration, the magnetic field generated by the electromagnet 11 is a magnetic field distribution that decreases outward in a radial direction of the orbit, the high frequency cavity 21 accelerates the ion up to a predetermined energy by the high frequency electric field adjusted to an orbital frequency in response to a nuclide of the incident ion, and a frequency of the high frequency electric field changes following an energy of the ion. Accordingly, it is possible to provide an accelerator and a particle therapy system capable shortening an irradiation time with a small size.

6 Claims, 10 Drawing Sheets

(51) Int. Cl.
   *H05H 13/04* (2006.01)
   *H05H 13/00* (2006.01)
   *H05H 7/08* (2006.01)

(52) U.S. Cl.
   CPC ............... *A61N 2005/1087* (2013.01); *H05H 2007/081* (2013.01); *H05H 2007/082* (2013.01)

(56) References Cited

U.S. PATENT DOCUMENTS

| | | | | |
|---|---|---|---|---|
| 8,144,832 B2* | 3/2012 | Balakin | .................. | H05H 13/04 378/65 |
| 8,188,688 B2* | 5/2012 | Balakin | .................... | H05H 7/04 315/503 |
| 8,421,031 B2* | 4/2013 | Honda | .................. | A61N 5/1043 250/398 |
| 8,421,041 B2* | 4/2013 | Balakin | .................... | H05H 7/04 250/492.3 |
| 8,466,441 B2* | 6/2013 | Iwata | .................... | A61N 5/1043 250/492.3 |
| 8,614,554 B2* | 12/2013 | Balakin | .................. | H05H 13/04 315/501 |
| 8,710,462 B2* | 4/2014 | Balakin | .................... | A61N 5/10 250/492.1 |
| 8,808,341 B2* | 8/2014 | Iwata | ........................ | A61B 5/08 607/1 |
| 8,841,866 B2* | 9/2014 | Balakin | .................... | G21K 1/14 315/500 |
| 9,579,525 B2* | 2/2017 | Balakin | .................. | H05H 13/04 |
| 9,649,510 B2* | 5/2017 | Balakin | .................... | A61N 5/107 |
| 9,694,207 B2* | 7/2017 | Iwata | .................... | A61N 5/1043 |
| 10,548,212 B2* | 1/2020 | Aoki | ..................... | A61N 5/1077 |
| 2010/0091948 A1* | 4/2010 | Balakin | .................. | H05H 13/04 378/65 |
| 2010/0266100 A1* | 10/2010 | Balakin | .................. | H05H 13/04 378/65 |
| 2011/0150180 A1* | 6/2011 | Balakin | .................. | G21K 1/087 378/65 |
| 2011/0182410 A1* | 7/2011 | Balakin | .................... | H05H 7/08 378/65 |
| 2012/0242257 A1* | 9/2012 | Balakin | .................... | H05H 7/04 315/503 |
| 2013/0253253 A1* | 9/2013 | Iwata | .................... | A61N 5/1049 600/1 |
| 2015/0005567 A1* | 1/2015 | Tsoupas | ............... | A61N 5/1077 600/1 |
| 2015/0084548 A1* | 3/2015 | Hara | .................... | H05H 13/005 315/501 |
| 2015/0115179 A1 | 4/2015 | Hiramoto et al. | | |
| 2015/0126798 A1* | 5/2015 | Iwata | .................... | A61N 5/1048 600/1 |
| 2015/0217139 A1* | 8/2015 | Bert | ...................... | A61N 5/1067 600/1 |
| 2016/0014877 A1* | 1/2016 | Sugahara | .................. | H05H 7/02 315/503 |
| 2017/0303384 A1 | 10/2017 | Aoki et al. | | |
| 2017/0339778 A1 | 11/2017 | Aoki et al. | | |
| 2019/0239334 A1* | 8/2019 | Aoki | ...................... | H01F 7/202 |

FOREIGN PATENT DOCUMENTS

WO    WO 2016/092621 A1    6/2016
WO    WO 2016/092623 A1    6/2016

* cited by examiner

ACCELERATOR AND PARTICLE THERAPY SYSTEM

TECHNICAL FIELD

The present invention relates to an accelerator for accelerating particles such as proton and carbon ions, and a particle therapy system for treating a tumor by irradiating the tumor with the accelerated particles.

BACKGROUND ART

In a charged particle beam system that irradiates a human body with a charged particle beam for treatment, as an example of the charged particle beam system that achieves high irradiation concentration and dose distribution control to a target while miniaturizing the system, in JP-A-2015-84886 (PTL 1), a plurality of types of ion beams having different weights are generated, an accelerator is used to accelerate and extract a plurality of types of ions to the highest energy having a different maximum underwater range, and the human body is irradiated from an irradiation system installed in a rotating gantry in a beam transport system. It is described that in the irradiation, the depth of the irradiation target is compared with the maximum underwater range of each ion species, and then the irradiation target is irradiated by selecting an ion species whose depth of the irradiation target is equal to or less than the maximum underwater range.

CITATION LIST

Patent Literature

PTL 1: JP-A-2015-84886

SUMMARY OF INVENTION

Technical Problem

A high energy atomic-nuclear beam used in particle therapy is generated by using an accelerator. For example, when a carbon nucleus is used as a therapeutic beam, a kinetic energy per nucleon is required at about 430 MeV at the maximum. When a proton is used as the therapeutic beam, the kinetic energy of about 230 MeV at the maximum is required.

In JP-A-2015-84886 (PTL 1), proposed is a system capable of generating beams of a plurality of nuclides with one accelerator and emitting a plurality of types of beams.

In the particle therapy system described in JP-A-2015-84886 (PTL 1), a synchrotron is used as the accelerator. The synchrotron increases the kinetic energy of particles orbiting inside while changing an excitation amount of an electromagnet forming the accelerator in time.

However, in addition to a bending magnet that bends the beam, the synchrotron is required to include various devices such as a quadrupole diverging magnet, a multipole magnet for resonance excitation, a high frequency application system for extracting the beam for increasing betatron oscillation to exceed a stability limit of resonance, an electrostatic deflector for extraction, and a bending magnet for extraction, and has limited miniaturization. Since various devices are required, there is a limit to cost reduction.

A cyclotron exists as the accelerator other than the synchrotron. However, the cyclotron is a type of accelerator that accelerates the beam orbiting in a main magnetic field with a high frequency electric field. An average magnetic field in the orbit is caused to be proportional to a relativistic γ factor of the beam, whereby the orbiting time is constant regardless of the energy. A main magnetic field distribution having this property is referred to as an isochronous magnetic field.

Here, the magnetic field is modulated along the orbit under the isochronous magnetic field, thereby securing the beam stability in a direction perpendicular to the inside of an orbital plane and the orbital plane. In order to achieve both the above-described isochronism and beam stability, the main magnetic field distribution requires a maximum part and a minimum part. A non-uniform magnetic field attached with this distribution can be formed by causing a distance between magnetic poles, which are opposite to each other, of the main electromagnet to be narrow at the maximum part and to be wide at the minimum part. However, a difference between a magnetic field at the maximum part and a magnetic field at the minimum part is practically limited to a degree of saturation magnetic flux density of a magnetic pole material which is a ferromagnetic material. That is, the difference between the magnetic field of the maximum part and the magnetic field of the minimum part is limited to about 2 T.

On the other hand, when the accelerator is miniaturized, it is required to increase the main magnetic field and reduce a bending radius of a beam orbit, but a difference between the main magnetic field, the magnetic field at the maximum part, and the magnetic field at the minimum part is proportional, and thus the aforementioned limit becomes a factor that determines a practical size of the accelerator. Therefore, it is difficult to perform the miniaturization of the cyclotron.

In the cyclotron, it is difficult to change the energy of the extracted beam without using a degrader. When the degrader is used, it is difficult to shorten an irradiation time because a beam current decreases.

The present invention provides an accelerator and a particle therapy system capable of shortening an irradiation time with a small size.

Solution to Problem

The present invention includes a plurality of systems for solving the above-described problems, and as an example, an accelerator includes: a plurality of ion sources that generate a plurality of different types of ions; a main magnet that generates a magnetic field; and a high frequency cavity that generates a high frequency electric field. The center of an orbit of the ion is eccentric with acceleration, the magnetic field generated by the main magnet is a magnetic field distribution that decreases outward in a radial direction of the orbit, the high frequency cavity accelerates the ion up to a predetermined energy by the high frequency electric field adjusted to an orbital frequency in response to a nuclide of the incident ion, and a frequency of the high frequency electric field changes following an energy of the ion.

Advantageous Effects of Invention

According to the present invention, it is possible not only to perform miniaturization of an accelerator, but also to shorten an irradiation time.

DESCRIPTION OF EMBODIMENTS

Hereinafter, an embodiment of an accelerator and a particle therapy system according to the present invention will be described with reference to the drawings.

First Embodiment

An accelerator according to a first embodiment, which is a desirable embodiment of the present invention, will be hereinafter described with reference to FIGS. 1 to 9.

An accelerator 1 of the embodiment is frequency modulation type variable energy and a variable nuclide accelerator. The accelerator 1 is a type of accelerator having a temporally constant magnetic field as a main magnetic field and accelerating a plurality of different types of ions such as a proton, helium, and carbon orbiting in the main magnetic field by a high frequency electric field. An appearance thereof is illustrated in FIG. 1.

Figure 1:
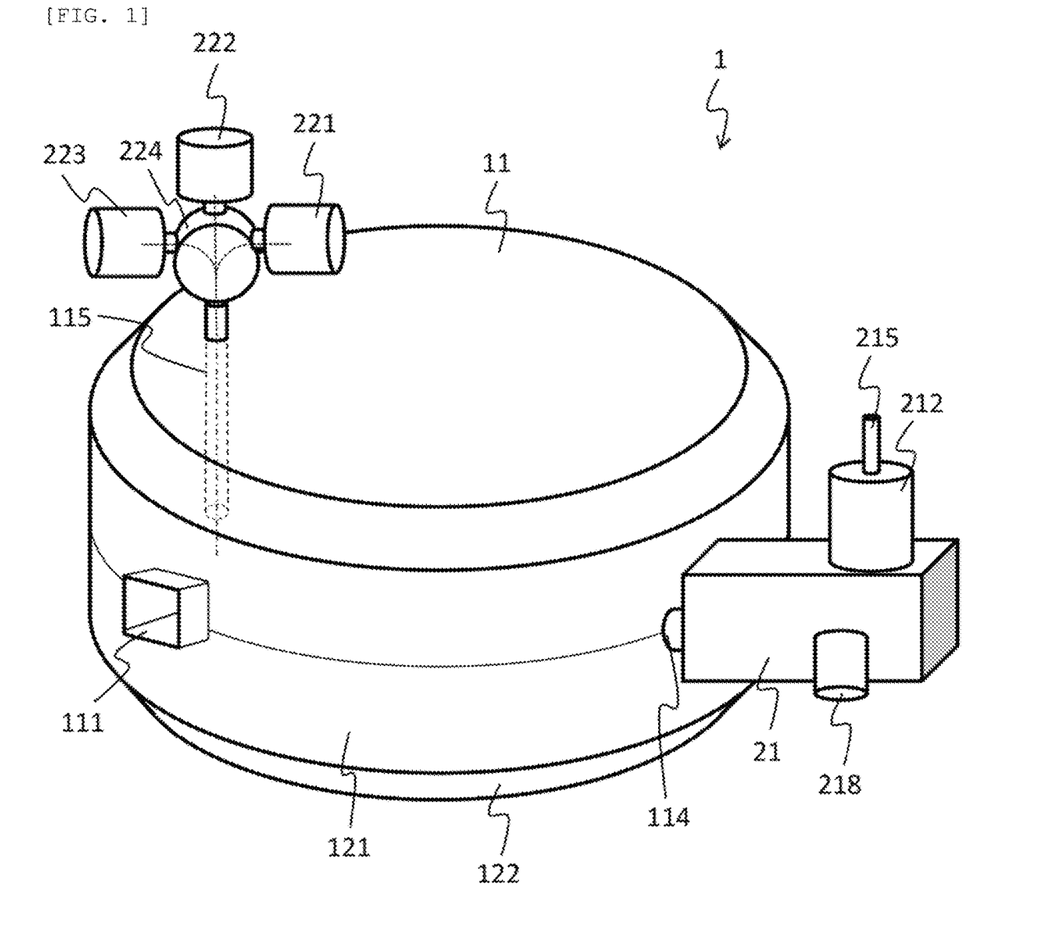
FIG. 1 illustrates an overall outline of an accelerator according to a first embodiment of the present invention.

As illustrated in FIG. 1, in the accelerator 1, the main magnetic field is excited in a region through which a beam being accelerated and orbiting passes (hereinafter, referred to as a beam passing region 20, refer to FIG. 2) by an electromagnet 11 that can be divided vertically. A plurality of through holes for connecting the outside and the beam passing region 20 are bored in the electromagnet 11.

As the through hole, an extraction beam through hole 111 for extracting the accelerated beam, through holes 112 and 113 for extracting a coil conductor to the outside, and a through hole for inputting high frequency power 114 are provided on a connection surface of the upper and lower magnetic poles. In the accelerator 1 of the embodiment, a high frequency cavity 21 is installed through the through hole for inputting high frequency power 114.

A dee electrode 211 for acceleration (refer to FIG. 2) and a rotary variable capacitance capacitor 212 are installed in the high frequency cavity 21 as described later.

On an upper part of the electromagnet 11, a plurality of ion sources 221, 222, and 223 for generating a plurality of different types of ions are installed at positions deviating from the center. An ion beam of a predetermined nuclide is incident on the inside of the accelerator 1 through a beam incident through hole 115.

The ion sources 221, 222, and 223 are external ion sources disposed outside the electromagnet 11, and are ion sources that respectively generate a proton, a helium ion, and a carbon ion.

Figure 2:
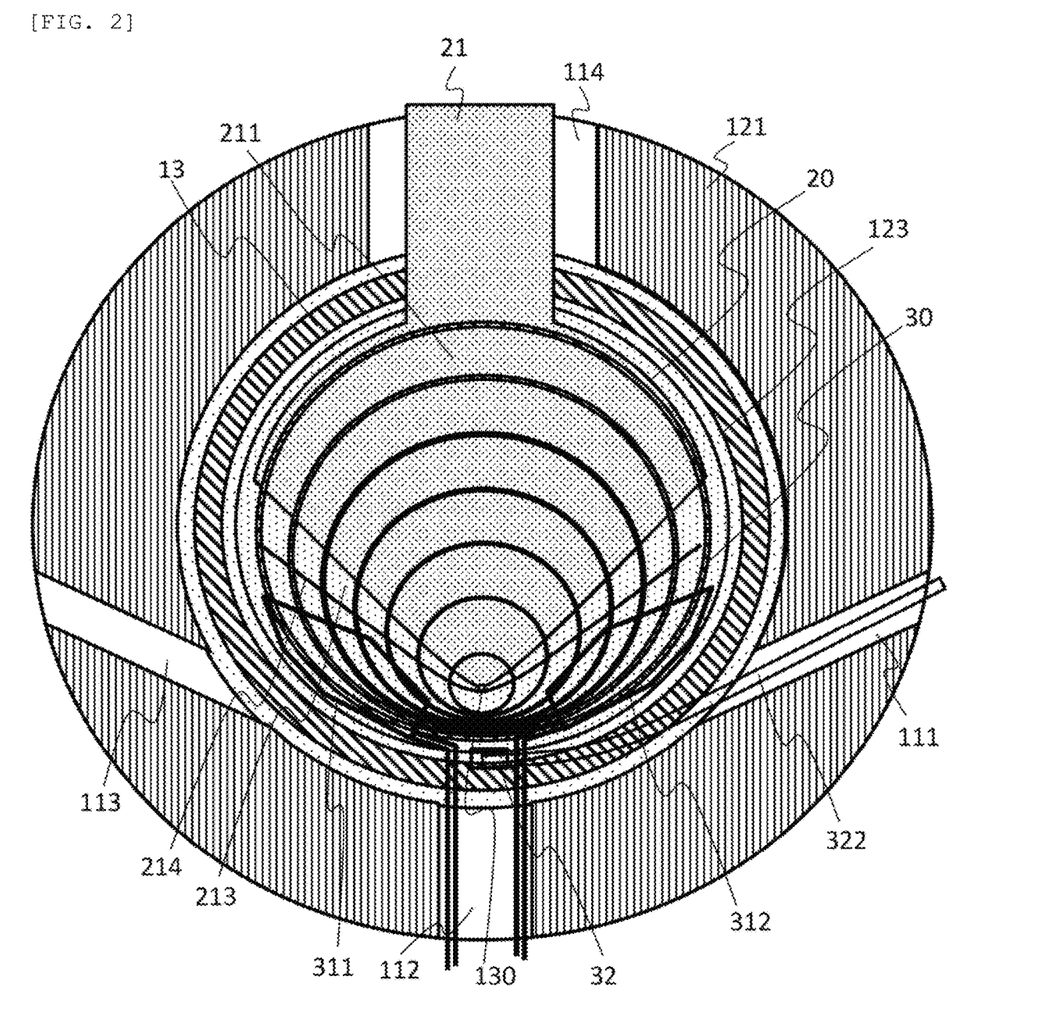
FIG. 2 is a diagram illustrating a structure of the accelerator according to the first embodiment.

A distribution magnet 224 for switching an ion nuclide is installed in the beam incident through hole 115 on a beam transport path from the ion sources 221, 222, and 223 to an incident region 130 of the accelerator 1 (refer to FIG. 2). In the accelerator 1 of the embodiment, an excitation amount of the distribution magnet 224 is adjusted so that a predetermined nuclide is transported on the beam transport path. That is, an ion species that can be incident on the accelerator 1 can be determined by the excitation amount of the distribution magnet 224.

The beam passing region 20 is evacuated.

Next, an internal structure of the accelerator will be described with reference to FIG. 2. FIG. 2 is a diagram in which the electromagnet 11 is divided vertically and viewed from above.

As illustrated in FIG. 2, each of the upper and lower parts of the electromagnet 11 includes a return yoke 121, a top plate 122, and a columnar magnetic pole 123, and includes the beam passing region 20 in a cylindrical space sandwiched by the magnetic poles 123 vertically opposite to each other. A plane where the upper and lower magnetic poles 123 are opposite to each other is defined as a magnetic pole plane. A plane parallel to the magnetic pole plane sandwiched between the magnetic pole planes and mutually at equal distances from the upper and lower magnetic pole planes is referred to as an orbital plane.

An annular main coil 13 is installed along a wall of the magnetic pole 123 in a recessed part formed between the magnetic pole 123 and the return yoke 121. When a current flows through the main coil 13, the magnetic pole 123 is magnetized, and a magnetic field having a predetermined distribution, which will be described later, is excited in the beam passing region 20.

A plurality of systems of trim coils 30 for fine adjustment of the magnetic field are provided in the magnetic pole 123, and are connected to an external power supply through the through hole 113. The exciting current is adjusted individually for each system, whereby a trim coil current is adjusted before an operation so as to approach a main magnetic field distribution, which will be described later, and to realize stable betatron oscillation.

The high frequency cavity 21 excites a high frequency electric field in an acceleration gap 213 by a $\lambda/4$ type resonance mode. A portion of the inside of the high frequency cavity 21, particularly a portion fixedly installed with respect to the accelerator, is defined as the dee electrode 211.

The beam is accelerated by the high frequency electric field excited by the acceleration gap 213 formed in a region sandwiched by the dee electrode 211 and a ground electrode 214 installed to be opposite to the dee electrode 211. In order to synchronize a phase of the high frequency electric field with the above-described orbit of the beam, the frequency of the high frequency electric field is required to be an integral multiple of an orbital frequency of the beam. In the accelerator 1, the frequency of the high frequency electric field is set to be one time the orbital frequency of the beam.

The beam is incident on the accelerator 1 from the incident region 130 in a state of a low energy ion. The ions generated by the ion sources 221, 222, and 223 are extracted to an incident path by a voltage applied to an extraction electrode (not illustrated), and are incident on the incident region 130 through the through hole 115.

An electrostatic deflector (not illustrated) is installed in the incident region 130, and electric power required for ion bending is supplied from the outside of the electromagnet 11. An incident beam is accelerated each time the incident beam passes through the acceleration gap 213 by the high frequency electric field excited by the high frequency cavity 21.

As a kicker magnetic field generating coil that is excited to extract the ion beam of a predetermined energy out of the accelerator 1, a second coil 311 and a first coil 312 are installed on the ion orbit in a state of being electrically insulated at a part of the magnetic pole plane. In the embodiment, a magnetic field, which will be escribed later, is superimposed and excited with respect to the main magnetic field by allowing a current to flow through the second coil 311 and the first coil 312. The details of the second coil 311 and the first coil 312 will be described later.

An incident part of an extraction septum magnet 32 is installed at one place of an end of the magnetic pole plane. The beam orbiting in the presence of the kicker magnetic field shifts its position from the designed orbit, and the beam moves up to the incident part of the extraction septum magnet 32, after which the beam is extracted out of the accelerator 1 along an extraction orbit 322 formed by the magnetic field of the extraction septum magnet 32.

In the accelerator 1 of the embodiment, a shape and an arrangement of the magnetic pole 123, the main coil 13, a trim coil 30, the kicker magnetic field generating coil, and the extraction septum magnet 32 are plane-symmetric with respect to the orbital plane so that an in-plane component of the main magnetic field is set to almost zero on the orbital plane. As illustrated in FIG. 2, the magnetic pole 123, the dee electrode 211, the main coil 13, the trim coil 30, and the kicker magnetic field generating coil have symmetrical shapes when the accelerator 1 is viewed from the upper part side.

Next, the orbit of the beam orbiting in the accelerator 1 of the embodiment will be described. The particles that can be accelerated by the accelerator 1 of the embodiment are protons, helium nuclei, and carbon nuclei.

Each ion beam is generated in the ion sources 221, 222, and 223 provided separately, and is transported up to the incident region 130 through the beam incident through hole 115 which is a common incident path.

The beam incident on the incident region 130 is bent by the electrostatic deflector in a direction parallel to the orbital plane, and starts orbital motion by the Lorentz force received from the main magnetic field. The beam performs the orbital motion along the designed orbit which will be described later.

The beam passes through the acceleration gap 213 twice each time the beam orbits one time in the accelerator 1, and the beam is accelerated by a force from the high frequency electric field each time the beam passes therethrough. As the kinetic energy increases, the orbital frequency of the beam decreases. The main magnetic field is uniform along the orbit of the beam, and generates a distribution in which the magnetic field decreases as the energy increases. That is, the magnetic field is formed such that the magnetic field outside in a radial direction decreases.

In such a magnetic field, the betatron oscillation is stably performed in each of the radial direction in the orbital plane of the beam and the direction perpendicular to the orbital plane. According to this principle, the beam is accelerated while orbiting in the beam passing region 20.

The magnitude of the main magnetic field in the incident region is 5 T; when the ion species is proton, the orbital frequency is 76.23 MHz in the ion of the kinetic energy immediately after the incidence; and the beam reaching the maximum energy of 235 MeV orbits at 60.67 MHz. In the case of helium, the frequency is 38.38 MHz immediately after the incidence and 30.44 MHz at the maximum energy of 235 MeV/u. In the case of carbon, the frequency is 38.40 MHz immediately after the incidence, and 26.10 MHz at the maximum energy of 430 MeV/u.

Figure 3:
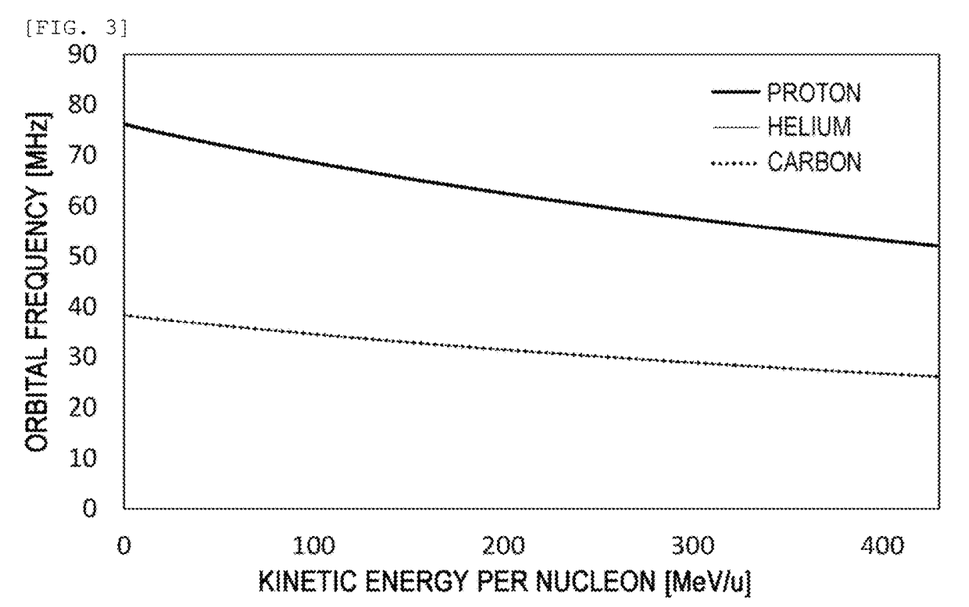
FIG. 3 is a diagram illustrating a relationship between a kinetic energy of a beam and an orbital frequency thereof in the accelerator according to the first embodiment.

A relationship between these energies and the orbital frequencies is illustrated in FIG. 3. FIG. 3 illustrates the frequency dependence of a proton with a thick line, helium with a thin line, and carbon with a dotted line. Since a mass-to-charge ratio of helium and carbon is almost equal, both graphs substantially appear to overlap in FIG. 3. It can also be regarded as the same in practical use.

The kinetic energy of the beam that can be extracted is from 70 MeV at the minimum to 235 MeV at the maximum when the ion species is the proton. In the case of Helium, the kinetic energy is from 70 MeV/u at the minimum to 235 MeV/u at the maximum. In the case of carbon, the kinetic energy is from 140 MeV/u at the minimum and 430 MeV/u at the maximum.

Figure 4:
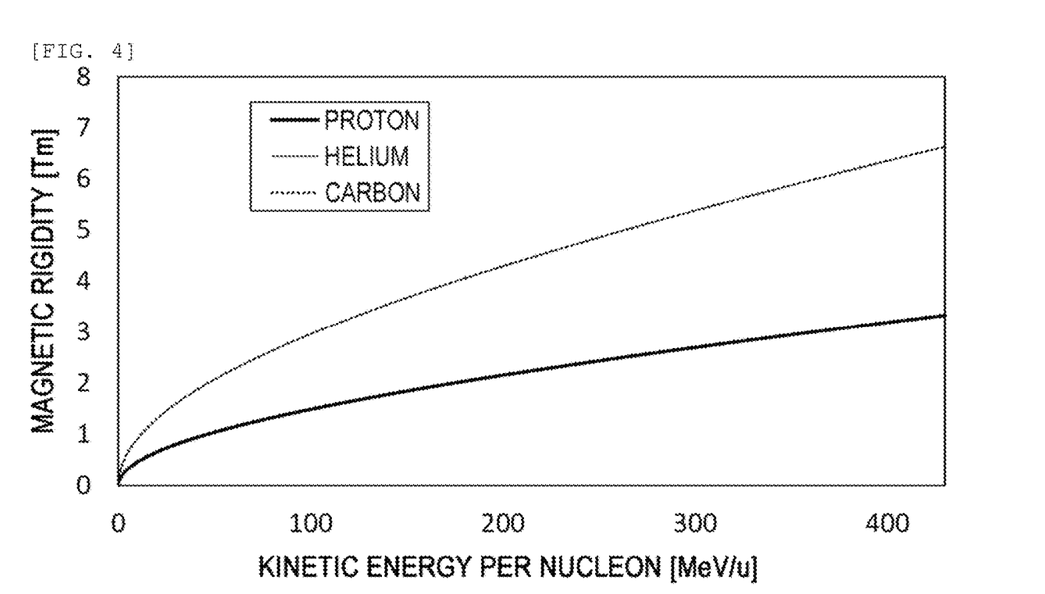
FIG. 4 is a diagram illustrating a relationship between the kinetic energy of the beam and magnetic rigidity thereof in the accelerator according to the first embodiment.

The orbits of the beams of these different ion species and the characteristics of betatron oscillation can be determined in a unified manner by magnetic rigidity. FIG. 4 illustrates a relationship between magnetic rigidity (Bρ value) and the kinetic energy of each ion.

According to FIG. 4, the maximum magnetic rigidity of the proton is 2.35 Tm, 4.67 Tm for helium, and 6.64 Tm for carbon. That is, the orbit is defined with respect to the beam having the magnetic rigidity of up to 6.64 Tm corresponding to the maximum magnetic rigidity of carbon, and the betatron oscillation is required to be stable.

Figure 5:
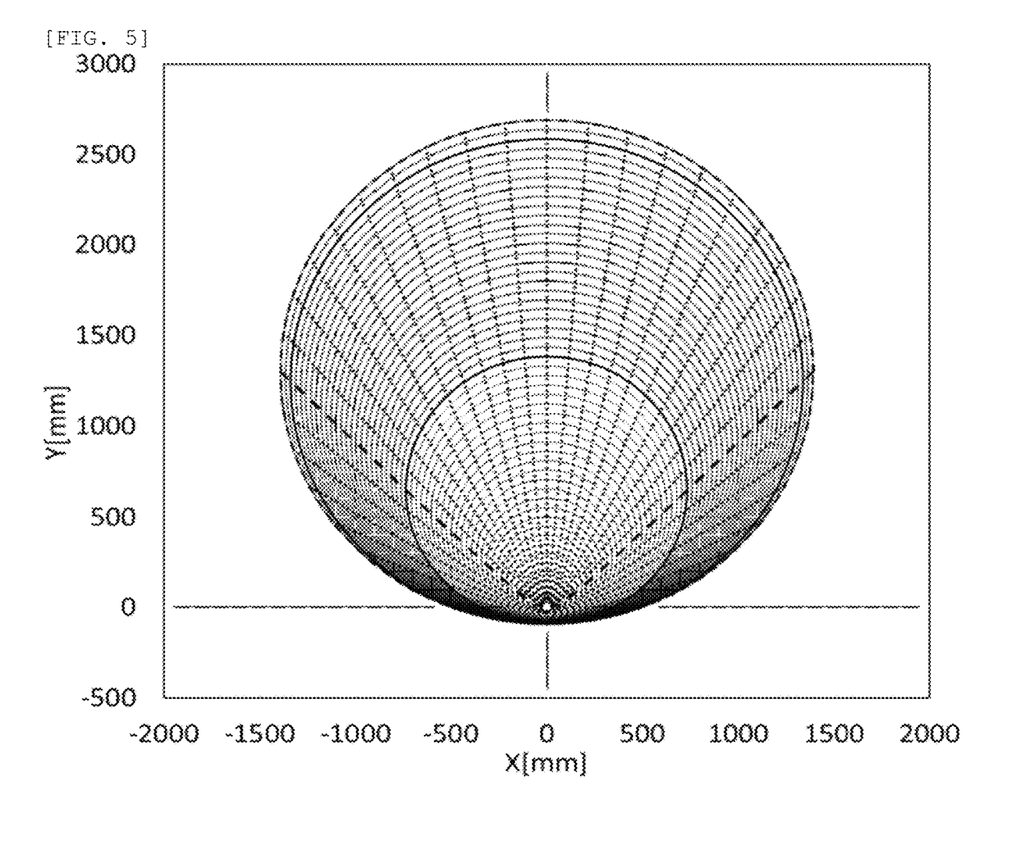
FIG. 5 is a diagram illustrating a shape of a designed orbit in the accelerator according to the first embodiment.

An orbital shape of each magnetic rigidity beam is illustrated in FIG. 5. As illustrated in FIG. 5, there exists a circular orbit having a radius of 1.39 m corresponding to the orbit having the maximum magnetic rigidity of 6.9 Tm on the outermost side, and from there, 52 circular orbits, which are divided into 53 with the magnetic rigidity up to 0 Tm, are illustrated. A dotted line or a broken line is a line connecting the same orbital phase of each orbit, and is referred to as an equal orbital phase line. The equal orbital phase line is plotted for each orbital phase π/20 from an aggregation region. What is indicated by a broken line among the equal orbital phase lines is a center position of the acceleration gap.

In the accelerator 1, the center of the orbit of the beam moves in one direction in the orbital plane according to the acceleration of the beam. As a result of the movement of the center of the orbit, there exist a region where the orbits of different kinetic energies are close to each other and a region which the orbits thereof are remote from each other. That is, the closed orbit of the beam is eccentric.

When respective points of the orbits where the orbits are closest to each other are connected to each other, the connected points become a line segment orthogonal to the orbit, and when respective points of the orbits where the orbits are farthest from each other are connected to each other, the connected points become a line segment orthogonal to the orbit. These two line segments exist on the same straight line. When this straight line is defined as a symmetry axis, the shape of the orbit and the distribution of the main magnetic field pass through the symmetry axis and are plane-symmetric with respect to a plane perpendicular to the orbital plane.

At each point of the above-described adjacent orbits, a coordinate θ is introduced so as to become a bending angle θ=0 degree. θ is the bending angle when viewed from a proximity point. The acceleration gap 213 formed between the ground electrodes 214 opposite to the dee electrode 211 in any orbit is installed along the equal orbital phase line that makes an orbit of ±90 degrees when viewed from an aggregation point.

In order to generate the above-mentioned orbit configuration and stable oscillation around the orbit, in the accelerator 1 of the embodiment, the designed orbit has a main magnetic field distribution in which the value of the magnetic field decreases as going outward in a bending radial direction. The magnetic field is constant along the designed orbit. Accordingly, the designed orbit becomes a circular shape, and its orbit radius and orbiting time increase as the beam energy increases.

In such a system, particles slightly deviating in the radial direction from the designed orbit receives a restoring force returning to the designed orbit. At the same time, a particle deviating in a direction perpendicular to the orbital plane also receives a restoring force from the main magnetic field in a direction returning to the orbital plane. In other words, when the magnetic field is appropriately reduced with respect to the beam energy, the particles always deviating from the designed orbit exerts the restoring force in the direction returning to the designed orbit, and the vicinity of the designed orbit is oscillated. Accordingly, the beam can be stably orbited and accelerated. The oscillation centering on this designed orbit is referred to as the betatron oscillation.

Figure 6:
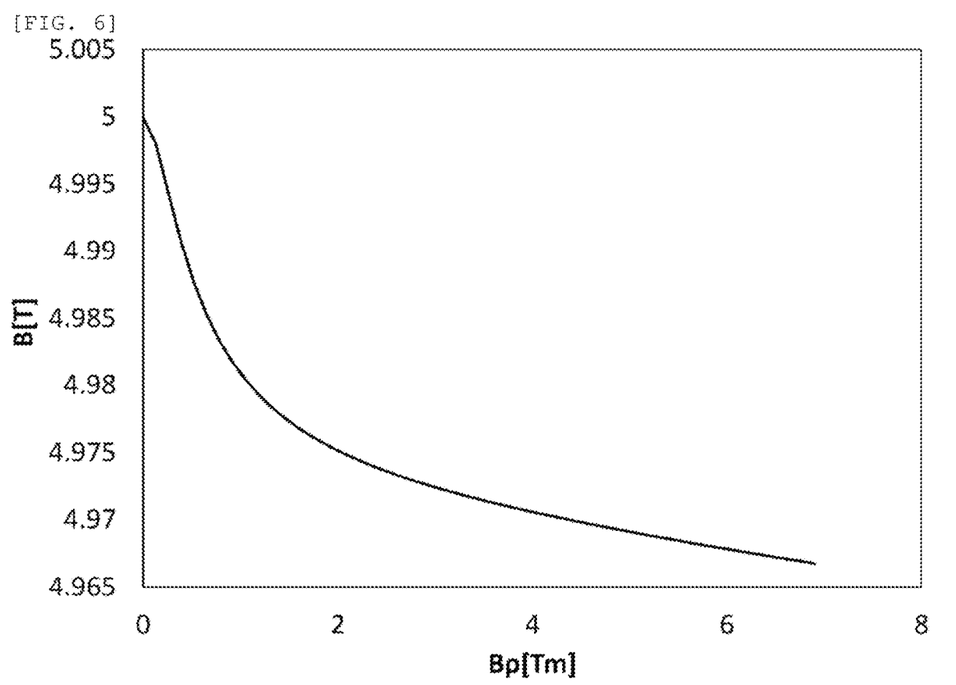
FIG. 6 is a diagram illustrating a relationship between the magnetic rigidity of the beam and a magnetic field on the designed orbit in the accelerator according to the first embodiment.

FIG. 6 illustrates a value of the magnetic field in the beam of each magnetic rigidity. As illustrated in FIG. 6, the magnetic field becomes 5 T at the maximum at the incident point and drops up to 4.966 T at the outermost periphery.

The above-described main magnetic field distribution is excited by magnetizing the magnetic pole 123 by allowing a predetermined exciting current to flow through the main coil 13 and the trim coil 30. In order to form a distribution in which the magnetic field increases at the ion incident point and the magnetic field decreases toward the outer periphery, a distance (gap) at which the magnetic poles 123 are opposite to each other is formed to be the smallest at the incident point and formed to become larger toward the outer periphery.

The magnetic pole shape is a plane-symmetric shape with respect to a plane (orbital plane) passing through the center of the gap, and has only a magnetic field component in a direction perpendicular to the orbital plane. Fine adjustment of the magnetic field distribution is performed by adjusting the current applied to the trim coil 30 installed on the magnetic pole plane, thereby exciting a predetermined magnetic field distribution.

The high frequency cavity 21 excites the high frequency electric field in the acceleration gap 213 by the λ/4 type resonance mode. In the accelerator 1 of the embodiment, in order to excite the high frequency electric field in synchronization with the orbit of the beam, the frequency of the high frequency electric field is modulated by following the energy of the orbiting beam.

In the high frequency cavity 21 using the resonance mode as used in the embodiment, it is required to sweep a high frequency in a range wider than a resonance width. Therefore, it is also required to change a resonance frequency of the high frequency cavity 21.

The control is performed by changing the electrostatic capacitance of the rotary variable capacitance capacitor 212 installed at the end of the high frequency cavity 21. The rotary variable capacitance capacitor 212 controls the electrostatic capacitance generated between a conductor plate directly connected to a rotating shaft 215 and an external conductor by a rotation angle of the rotating shaft 215. That is, the rotation angle of the rotating shaft 215 is changed with the acceleration of the beam.

The behavior of the beam from beam incidence to beam extraction in the accelerator 1 according to the embodiment will be hereinafter described.

First, a driver inputs a desired ion nuclide and kinetic energy to an overall control system 40. The overall control system 40 operates the ion sources 221, 222, and 223 and sets the excitation amount of the distribution magnet 224 so that the ion beam is outputted from the ion source of the designated nuclide, and the beam is guided to the beam passing region 20.

As described above, since the orbital frequency at the time of incidence is different depending on the nuclide, the angle of the rotating shaft 215 suitable for incidence is different. Therefore, based upon the signal from a rotation angle sensor 216 (refer to FIG. 7), the ions are outputted from the ion sources 221, 222, and 223 at the timing when the resonance frequency of the high frequency cavity 21 coincides with the orbital frequency at the time of incidence.

While the beam incident on the beam passing region 20 is accelerated by the high frequency electric field, its energy increases and a rotation radius of the orbit increases.

Thereafter, the beam is accelerated while maintaining the stability in a traveling direction by the high frequency electric field. That is, when the high frequency electric field temporally decreases, the beam passes though the acceleration gap 213. Accordingly, since the frequency of the high frequency electric field and the orbital frequency of the beam are synchronized at a ratio of exactly an integral multiple (one time in the embodiment), particles accelerated at a phase of a predetermined accelerating electric field is also accelerated at the same phase in the next turn. On the other hand, since particles accelerated in a phase earlier than the acceleration phase have a larger amount of acceleration than the particles accelerated in the acceleration phase, the particles are accelerated in a delayed phase in the next turn. Conversely, since particles accelerated in a phase slower than the acceleration phase in some cases has a smaller amount of acceleration than the particles accelerated in the acceleration phase, the particles are accelerated at an advanced phase in the next turn.

As described above, the particles at the timing deviating from a predetermined acceleration phase moves in a direction returning to the acceleration phase, and by this action, it is possible for the particles to stably oscillate even in a phase plane (traveling direction) formed of the momentum and the phase. This oscillation is referred to as synchrotron oscillation. That is, the particles during acceleration are gradually accelerated while performing the synchrotron oscillation, and reaches a predetermined energy to be extracted.

In order to extract the particles at the predetermined energy, a predetermined exciting current determined based upon a target energy is caused to flow through a kicker magnetic field generating coil. The beam accelerated up to the target energy orbits along its designed orbit when the current does not flow through the kicker magnetic field generating coil, but when the current flows through the kicker magnetic field generating coil, the beam is kicked by a magnetic field derived from the kicker magnetic field generating coil, and displaced from the designed orbit.

The kicker magnetic field generating coil is installed symmetrically with respect to the orbital plane at a position deviating in the direction perpendicular to the orbital plane. The kicker magnetic field generating coil has a shape symmetrical with respect to a straight line (symmetrical axis) connecting a most densely aggregated point of the beam orbit and a sparsely dispersed point thereof.

The first coil 312 and the second coil 311 forming the kicker magnetic field generating coil are respectively connected to separate kicker magnetic field generating coil power supplies 44A and 44B (refer to FIG. 7), and the directions of the currents are controlled so as to generate the magnetic fields in directions opposite to each other.

A current flows through the first coil 312 so as to generate the magnetic field in the same direction with respect to the main magnetic field, and a current flows through the second coil 311 so as to generate a magnetic field in a direction opposite to the main magnetic field. The first coil 312 is generally referred to as a regenerator, and the second coil 311 is generally referred to as a peeler.

In this manner, when the regenerator is configured to provide the kick inside the beam radial direction at a certain position during the orbit, and the peeler is configured to provide the kick outside the radial direction further downstream, in the accelerator 1 of the embodiment in which the tune is close to 1, the radial direction displacement between the peeler and the regenerator increases.

The beam receives the kicks from the peeler and the regenerator over a plurality of turns, the radial direction side of the beam at a position of the aggregation point continues to increase. When the radial direction displacement increases to some extent, the beam is incident on the extraction septum magnet 32 installed outside the aggregation point, and is extracted out of the accelerator 1.

Figure 7:
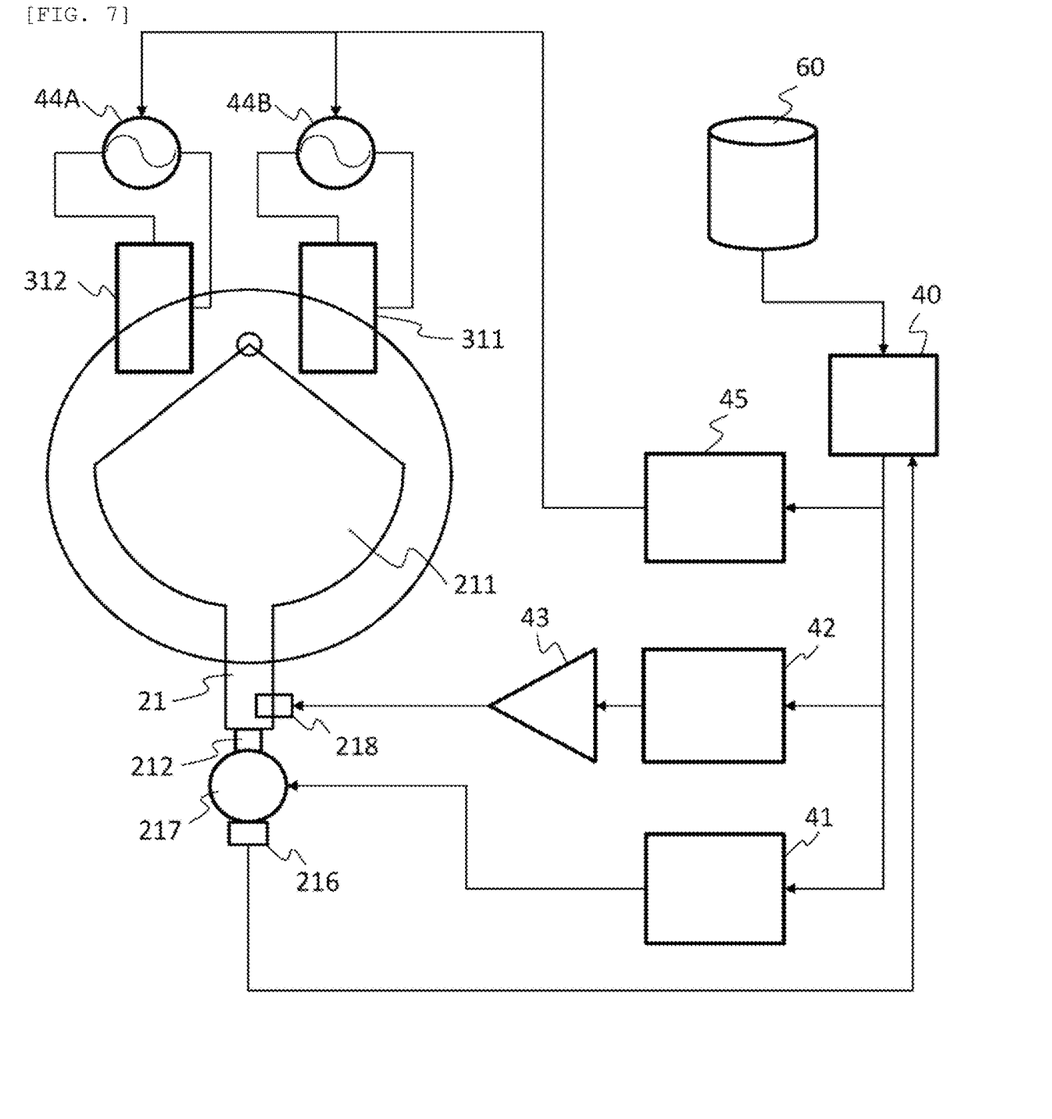
FIG. 7 is a diagram illustrating a control diagram in the accelerator according to the first embodiment.

A control diagram and an operation flow of each device when the beam is accelerated by the above-described principle and is extracted out of the accelerator 1 will be hereinafter described with reference to FIGS. 7, 8, and 9. FIG. 7 illustrates a control diagram of the accelerator 1 of the embodiment.

As illustrated in FIG. 7, a configuration for accelerating the beam and a control system thereof include: the rotary variable capacitance capacitor 212 attached to the high frequency cavity 21; a motor 217 connected to the rotating shaft 215 of the rotary variable capacitance capacitor 212; and a motor control system 41 for controlling the motor 217. The configuration and the control system further include: an input coupler 218 for inputting high frequency power to the high frequency cavity 21; a low-level high frequency generator 42 for generating the high frequency power to be supplied; and an amplifier 43.

In the rotary variable capacitance capacitor 212, determination is performed by a treatment planning database 60, control is performed by the motor control system 41 instructed by the overall control system 40, the rotating shaft 215 rotates by rotating the motor 217 at a predetermined rotation speed, and the capacitance is temporally modulated by changing the rotation angle of the rotating shaft 215 over time.

A high frequency signal generated by the low-level high frequency generator 42 is amplified by the amplifier 43, thereby generating the high frequency power to be inputted to the high frequency cavity 21. The frequency and amplitude of the high frequency signal generated in the low-level high frequency generator 42 are determined by the treatment planning database 60 and are instructed by the overall control system 40.

As illustrated in FIG. 7, a configuration for extracting the beam out of the accelerator 1 and a control system thereof include: the kicker magnetic field generating coil power supply 44A for supplying a current to the first coil 312; the kicker magnetic field generating coil power supply 44B for supplying a current to the second coil 311; a control system for the kicker magnetic field generating coil power supply 45 for controlling the kicker magnetic field generating coil power supplies 44A and 44B.

Current values outputted from the kicker magnetic field generating coil power supplies 44A and 44B to the first coil 312 and the second coil 311 are controlled by the control system for the kicker magnetic field generating coil power supply 45, the designated value is determined by the treatment planning database 60 as a value uniquely determined from the magnetic rigidity of the extracted beam, and designated value is instructed by the overall control system 40.

In the control system of the above-described accelerator 1, an operation (operation method) of each device when a beam having a certain magnetic rigidity is extracted will be described with reference to FIGS. 8 and 9. FIG. 7 is a timing chart of the operation of each device.

Figure 8:
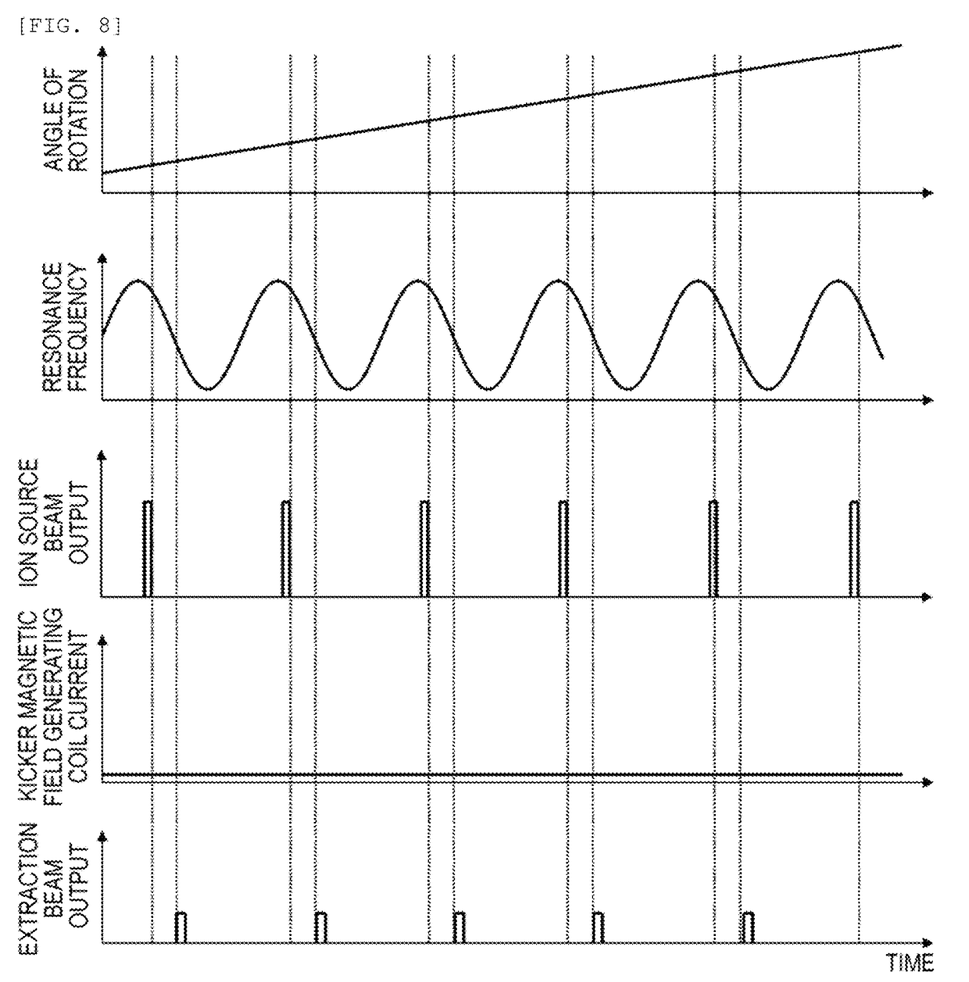
FIG. 8 is a diagram illustrating an example of a timing chart during an operation of the accelerator according to the first embodiment.
Figure 9:
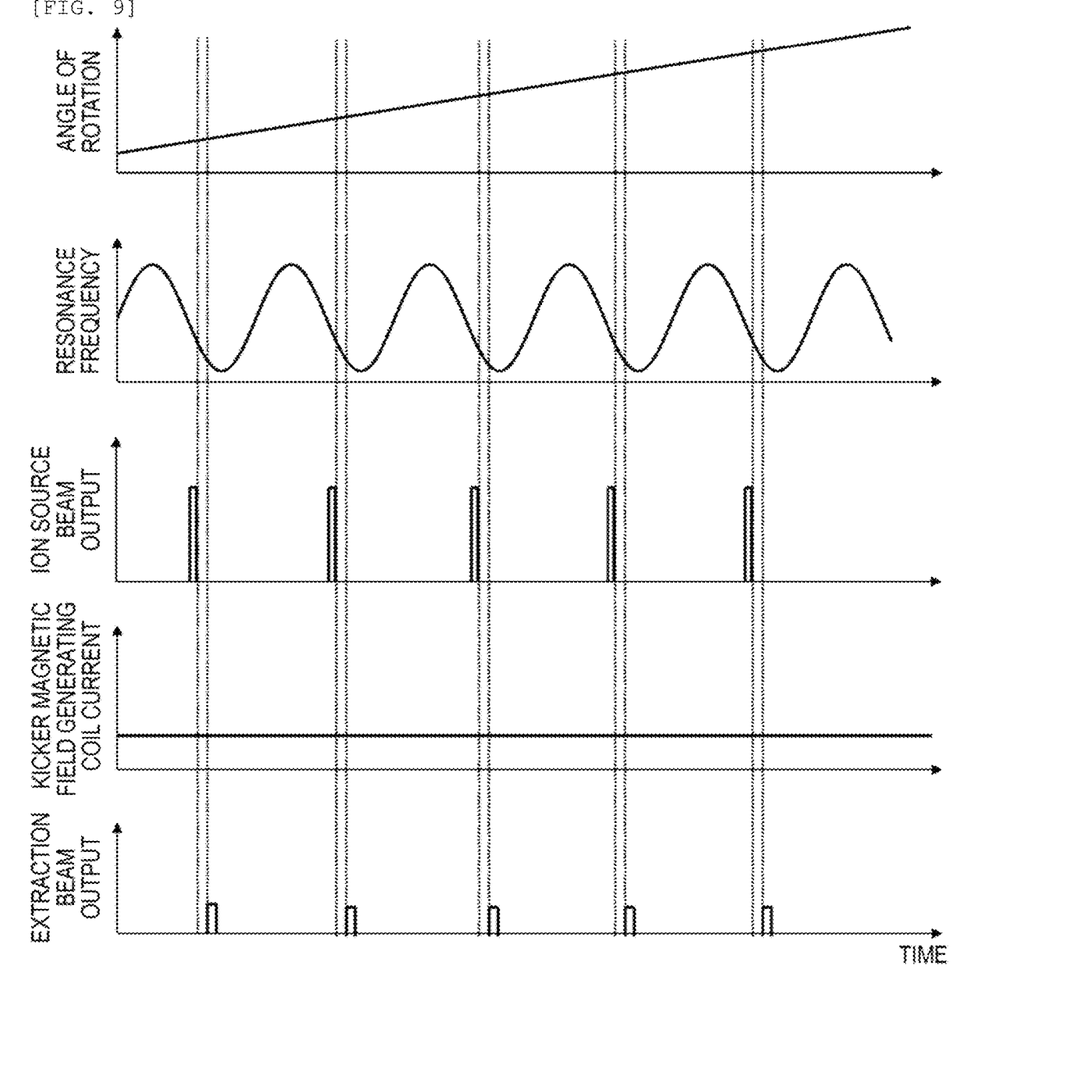
FIG. 9 is a diagram illustrating the example of the timing chart during the operation of the accelerator according to the first embodiment.

FIG. 8 illustrates a timing chart of the operation of each device when extracting a proton beam having a certain magnetic rigidity, and FIG. 9 illustrates a timing chart of the operation of each device when extracting a carbon beam.

FIGS. 8 and 9 illustrate a rotation angle of the rotating shaft of the variable capacitance capacitor 212; a resonance frequency of the high frequency cavity 21; beam current waveforms outputted by the ion sources 221, 222, and 223; a time chart of a current flowing through the kicker magnetic field generating coil; and a beam current waveform outputted from the accelerator 1. All the horizontal axes in FIGS. 8 and 9 are time.

First, as described above, the resonance frequency of the high frequency cavity 21 is periodically changed by the rotation angle of the rotating shaft of the variable capacitance capacitor 212. In accordance with this, the frequency of the high frequency signal outputted from the low-level high frequency generator 42 is synchronously changed. A period from the time when the resonance frequency becomes maximum to the time when the resonance frequency becomes the next maximum is defined as an operation cycle.

When the nuclide is a proton, the beam output from the ion source starts immediately after the start of the operation cycle as illustrated in FIG. 8.

On the other hand, in the case of carbon, as illustrated in FIG. 9, the beam output from the ion source starts at the timing when the resonance frequency drops to 38.38 MHz.

When receiving the acceleration, the beam incident within a range where stable synchrotron oscillation can be performed is continuously accelerated, but the beam whose synchrotron oscillation is not stable is not accelerated and collides with a structure inside the accelerator 1 to be lost.

The beam is accelerated as the resonance frequency decreases, and is accelerated to a vicinity of a predetermined extraction energy. The beam accelerated to the vicinity of the predetermined energy is kicked by the magnetic field from the first coil 312 and the second coil 311, and the displacement at the aggregation point starts to deviate outward in the radial direction. When the beam is further accelerated and reaches the predetermined energy, the beam enters the extraction septum magnet 32 and is thereafter extracted.

Next, effects of the embodiment will be described.

The above-described accelerator 1 according to the first embodiment of the present invention includes: the plurality of ion sources 221, 222, and 223 for generating a plurality of different types of ions; the electromagnet 11 for generating the magnetic field; and the high frequency cavity 21 for generating the high frequency electric field. The center of the ion orbit is eccentric with acceleration, the magnetic field generated by the electromagnet 11 has the magnetic field distribution that decreases outward in the radial direction of the orbit, the high frequency cavity 21 accelerates the ion up to the predetermined energy by the high frequency electric field adjusted to the orbital frequency in response to the nuclide of the incident ion, and the frequency of the high frequency electric field is changed following the energy of the ion.

The accelerator 1 of this principle can be formed as a compact accelerator because the main magnetic field can be a static magnetic field and a high magnetic field can be easily achieved as compared with a synchrotron of a related art.

In the synchrotron of the related art described in JP-A-2015-84886 (PTL 1), a linear accelerator is used as an incident system, and the beam is accelerated by a scheme in which the beam is incident on the synchrotron from the linear accelerator through a low energy beam transport. Therefore, when the nuclide is changed, it is required to change the type of the ion source and the acceleration electric field of the linear accelerator, the amount of excitation of the electromagnet of the beam transport system, the magnetic field and frequency of the synchrotron, and a relationship therebetween, and thus it is considered that it will take several seconds to switch the nuclide.

On the other hand, according to the accelerator 1 of the embodiment, in the case of nuclide switching, for example, only the amount of excitation of the kicker magnetic field generating coil and the ion incident timing are changed because the magnetic rigidity of the electromagnet in the above-described ion incident path and the extracted beam is necessarily changed. In other words, since the nuclide can be changed only by changing the amount of electromagnet excitation and the timing of operation, it is also possible to change the nuclide in the time of about several hundred ms required for changing the energy.

By the above-described characteristics, the accelerator 1 which is compact and has a large average beam amount can be provided by compactness by applying the high magnetic field, operation cycle shortening by applying the static magnetic field, and shortening of nuclide change time.

Since the ion sources 221, 222, and 223 are arranged outside the electromagnet 11, it is not required to arrange a plurality of ion sources in the beam passing region 20, and it is possible to more surely reduce the size of the electromagnet 11 and the accelerator 1.

Since the first coil 312 and the second coil 311 for generating the magnetic field for extracting the ion of the predetermined energy are further provided on the orbit of the ion such that the betatron oscillation in the closed orbit plane can be destabilized with respect to the beam having the specific energy to be extracted, a beam of arbitrary energy can be extracted. Therefore, since the energy variable beam can be extracted without using a scatterer, a beam current value lost at the time of extraction can be kept to the minimum, and thus a high irradiation dose rate can be realized. Since the beam extraction energy can be changed electrically, there is also an advantage that the time required for energy switching is shorter than that of a method of mechanically moving the scatterer.

The distribution magnet 224 disposed on the beam incident through hole 115 between the ion sources 221, 222, and 223 and the electromagnet 11 is further provided, thereby making it possible to switch the ion with high accuracy with a simple configuration.

In the embodiment, a case in which the switching of ion species of a plurality of types of nuclides is performed by the distribution magnet 224 is described, but the switching is not limited to the magnetic field using the electromagnet, and the switching can be also performed by an electric field using an electrode.

Second Embodiment

A particle therapy system according to a second embodiment, which is a desirable embodiment of the present invention, will be described with reference to FIG. 10. The same components as those of the first embodiment will be denoted by the same reference signs, and the description thereof will be omitted.

The second embodiment is a particle therapy system using the accelerator 1 described in the first embodiment. FIG. 10 illustrates an overall configuration diagram of the system.

Figure 10:
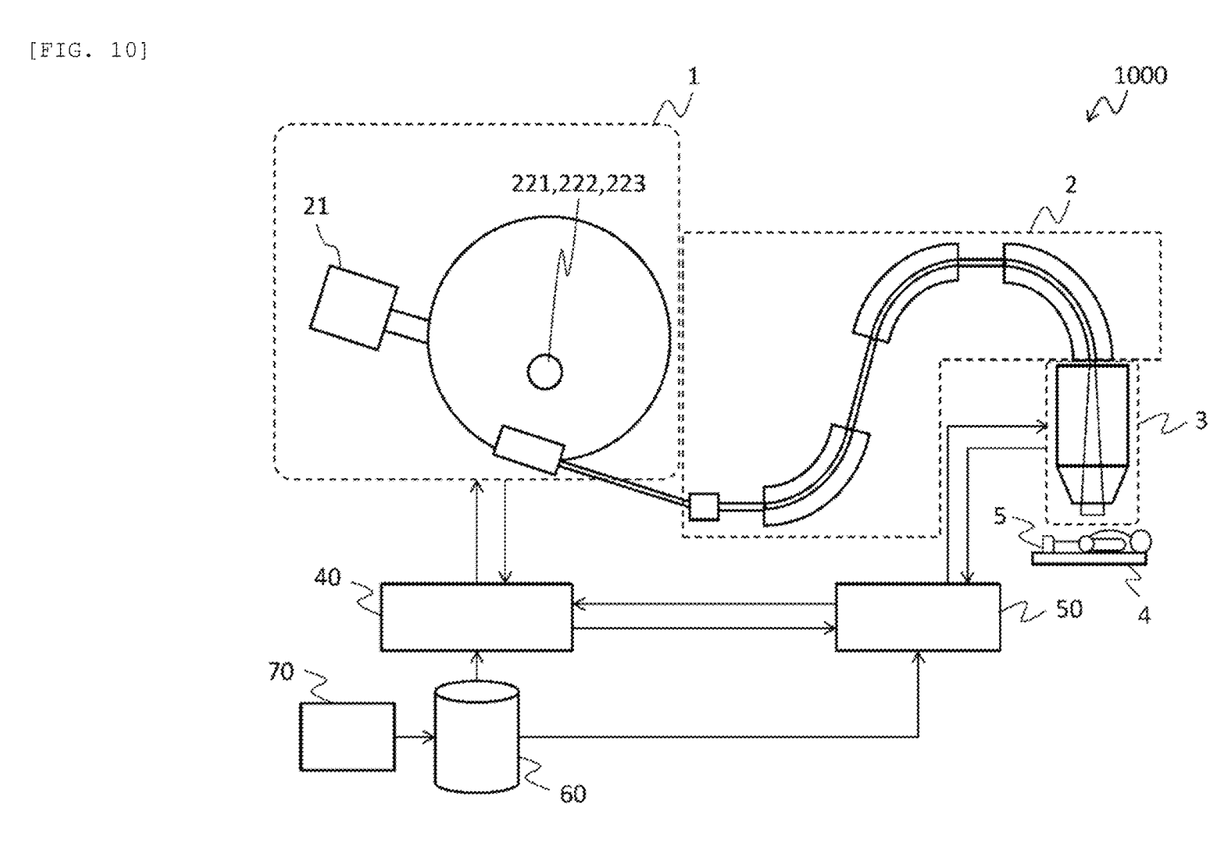
FIG. 10 is a diagram illustrating an overall outline of a particle therapy system according to a second embodiment.

As illustrated in FIG. 10, a particle therapy system 1000 is a system that irradiates a patient with the energy of a proton beam, a helium beam, or a carbon beam (hereinafter, collectively referred to as a beam) to be emitted depending on the depth from a body surface of a target volume at an appropriate value.

The particle therapy system 1000 includes: the accelerator 1 for accelerating the ion; a beam transport system 2 for transporting the beam accelerated by the accelerator 1 to an irradiation system which will be escribed later; an irradiation system 3 for irradiating a target in a patient 5 fixed to a treatment table 4 with the beam transported by the beam transport system 2; the overall control system 40 and an irradiation control system 50 for controlling the accelerator 1, the beam transport system 2, and the irradiation system 3; a treatment planning system 70 for generating a beam emission planning for the target; and the treatment planning database 60 for storing the treatment planning generated by the treatment planning system 70.

In the particle therapy system 1000, the energy and dose of the emitted particle beam are generated by the treatment planning system 70, and determined by the treatment planning stored in the treatment planning database 60. The energy and emission amount of the particle beam determined by the treatment planning are sequentially inputted from the overall control system 40 to the irradiation control system 50, and then transferred to the next energy or the next nuclide when the appropriate irradiation amount is emitted, after which the particle beam is emitted again, thereby realizing a procedure of the system.

According to the particle therapy system of the second embodiment of the present invention, a compact and high throughput system can be realized by utilizing the compactness and the size of an average beam amount which are the above-described characteristics of the accelerator 1 of the first embodiment.

The beam transport system 2 of the particle therapy system 1000 is not limited to a fixed one as illustrated in FIG. 10, and can be a transport system capable of rotating around the patient 5 together with the irradiation system 3 referred to as a rotating gantry. The irradiation system 3 is not limited to one, and a plurality of irradiation systems can be provided. The beam can be directly transported from the accelerator 1 to the irradiation system 3 without providing the beam transport system 2.

Others

The present invention is not limited to the above-described embodiments, but includes various modifications. The above-described embodiments are described in detail in order to describe the present invention for easy understanding, and are not necessarily limited to those including all the configurations described above.

For example, three types of the proton, helium, and carbon are described as a plurality of types of ions to be accelerated by the accelerator 1, but the ions to be accelerated are not limited to these three types, and various types of ions can be accelerated. It is not required to use three types, but two or more types can be used.

REFERENCE SIGNS LIST

1: accelerator
11: electromagnet
111: extraction beam through hole
112, 113: through hole for coil connection
114: through hole for inputting high frequency power
115: beam incident through hole
13: main coil
121: return yoke
122: top plate
123: magnetic pole
130: incident region
20: beam passing region
21: high frequency cavity
211: dee electrode
212: rotary variable capacitance capacitor
213: acceleration gap
214: ground electrode
215: rotating shaft
216: rotation angle sensor
217: motor
218: input coupler
221, 222, 223: ion source
224: distribution magnet
30: trim coil
311: second coil (kicker magnetic field generating coil)
312: first coil (kicker magnetic field generating coil)
32: extraction septum magnet
321: extraction orbit
40: overall control system
41: motor control system
42: low-level high frequency generator
43: amplifier
44A, 44B: kicker magnetic field generating coil power supply
45: coil power supply control system for generating the kicker magnetic field
50: irradiation control system
60: treatment planning database
70: treatment planning system
1000: particle therapy system

The invention claimed is:

1. An accelerator, comprising:
   a plurality of ion sources that generate a plurality of different types of ions;
   a main magnet that generates a magnetic field; and
   a high frequency cavity that generates a high frequency electric field, wherein
   a center of an orbit of the ion is eccentric with acceleration,
   the magnetic field generated by the main magnet is a magnetic field distribution that decreases outward in a radial direction of the orbit,
   the high frequency cavity accelerates the ion up to a predetermined energy by the high frequency electric field adjusted to an orbital frequency in response to a nuclide of the incident ion, and
   a frequency of the high frequency electric field changes following an energy of the ion.

2. The accelerator according to claim 1, wherein the ion source is arranged outside the main magnet.

3. The accelerator according to claim 1, further comprising:
   a coil that generates a magnetic field for extracting the ion of a predetermined energy on the orbit of the ion.

4. The accelerator according to claim 1, further comprising:
   a distribution magnet arranged in a beam transport path between the ion source and the main magnet.

5. A particle therapy system using an accelerator as a beam source, wherein the accelerator according to claim 1 is used as the beam source.

6. The accelerator according to claim 1, further comprising at least one acceleration gap disposed in between a plurality of electrodes.

* * * * *